United States Patent
Barak et al.

(10) Patent No.: US 12,031,850 B2
(45) Date of Patent: Jul. 9, 2024

(54) MAGNETIC LOCALIZATION USING A DC MAGNETOMETER

(71) Applicant: Magnisity Ltd., Hod-HaSharon (IL)

(72) Inventors: Ron Barak, Tel-Aviv (IL); Ariel Birenbaum, RaAnana (IL); Benjamin Greenburg, Hod-HaSharon (IL)

(73) Assignee: Magnisity Ltd., Hod-HaSharon (IL)

( * ) Notice: Subject to any disclaimer, the term of this patent is extended or adjusted under 35 U.S.C. 154(b) by 157 days.

(21) Appl. No.: 17/414,377

(22) PCT Filed: Dec. 12, 2019

(86) PCT No.: PCT/IL2019/051363
§ 371 (c)(1),
(2) Date: Jun. 16, 2021

(87) PCT Pub. No.: WO2020/129050
PCT Pub. Date: Jun. 25, 2020

(65) Prior Publication Data
US 2022/0065661 A1    Mar. 3, 2022

Related U.S. Application Data

(60) Provisional application No. 62/897,599, filed on Sep. 9, 2019, provisional application No. 62/780,291, filed on Dec. 16, 2018.

(51) Int. Cl.
*G01D 5/20* (2006.01)
*A61B 5/06* (2006.01)
(Continued)

(52) U.S. Cl.
CPC ............. *G01D 5/20* (2013.01); *G01C 19/00* (2013.01); *G01P 15/08* (2013.01); *A61B 5/062* (2013.01)

(58) Field of Classification Search
CPC ........... G01D 5/20; G01C 19/00; G01P 15/08; A61B 5/062; A61B 5/725;
(Continued)

(56) References Cited

U.S. PATENT DOCUMENTS

| 4,710,708 A | 12/1987 | Rorden et al. |
| 5,307,072 A | 4/1994 | Jones, Jr. |

(Continued)

FOREIGN PATENT DOCUMENTS

| EP | 2849669 | 3/2015 |
| JP | 2011-059091 | 3/2011 |

(Continued)

OTHER PUBLICATIONS

Final Official Action together with Interview Summary dated Oct. 17, 2022 From the US Patent and Trademark Office Re. U.S. Appl. No. 17/681,789. (35 Pages).

(Continued)

*Primary Examiner* — Akm Zakaria

(57) ABSTRACT

A magnetic localization system including a magnetic field generator that generates an alternating magnetic field with a maintained frequency; and a receiver comprising: a DC magnetometer to sense a local magnetic field, at least in part due to the generated magnetic field; and at least one processor that calculates a six-degrees-of-freedom (6DOF) position and orientation of the receiver relative to the generator, based on the sensed magnetic field and the maintained frequency, and optionally based on the momentary phase of the generated field. Optionally, the generator includes an actuator that applies a rotational motion; at least one magnet rotating about a first axis by the actuator; a magnetometer to sense a momentary rotation phase of the at least one magnet; and a controller to maintain a desired rotation frequency of the at least one magnet. Optionally, the (Continued)

generator communicates the maintained rotation frequency and optionally the sensed momentary phase.

20 Claims, 3 Drawing Sheets

(51) Int. Cl.
    *G01C 19/00*     (2013.01)
    *G01P 15/08*     (2006.01)

(58) Field of Classification Search
    CPC .. A61B 2017/00398; A61B 2034/2048; A61B 2034/2051; A61B 2034/2059; A61B 5/067; A61B 34/20; G01B 7/003; G01R 33/0017; G01R 33/0076; G01R 33/038; G01R 33/072; G01R 33/091
    See application file for complete search history.

(56) References Cited

U.S. PATENT DOCUMENTS

| | | | | |
|---|---|---|---|---|
| 5,347,289 | A * | 9/1994 | Elhardt | G01S 5/0247 |
| | | | | 701/530 |
| 5,646,525 | A | 7/1997 | Gilboa | |
| 5,769,843 | A | 6/1998 | Abela et al. | |
| 6,052,610 | A | 4/2000 | Koch | |
| 6,073,043 | A | 6/2000 | Schneider | |
| 6,833,814 | B2 | 12/2004 | Gilboa et al. | |
| 7,536,909 | B2 | 5/2009 | Zhao et al. | |
| 8,340,686 | B2 * | 12/2012 | Bartlett | G01S 5/0284 |
| | | | | 342/357.77 |
| 8,683,707 | B1 * | 4/2014 | Horton, Jr. | G01C 21/206 |
| | | | | 33/355 R |
| 8,825,134 | B2 | 9/2014 | Danehorn | |
| 9,024,624 | B2 | 5/2015 | Brunner | |
| 9,116,198 | B2 | 8/2015 | Cai et al. | |
| 9,658,298 | B2 | 5/2017 | Cai et al. | |
| 9,763,741 | B2 | 9/2017 | Alvarez et al. | |
| 9,839,481 | B2 | 12/2017 | Blumenkranz et al. | |
| 10,276,289 | B1 | 4/2019 | Kirby et al. | |
| 10,499,993 | B2 | 12/2019 | Chopra et al. | |
| 10,524,641 | B2 | 1/2020 | Prisco | |
| 10,610,306 | B2 | 4/2020 | Chopra | |
| 10,615,500 | B2 | 4/2020 | Morgan et al. | |
| 10,704,929 | B1 | 7/2020 | Memarzanjany et al. | |
| 2002/0065455 | A1 | 5/2002 | Ben-Haim et al. | |
| 2003/0216639 | A1 | 11/2003 | Gilboa et al. | |
| 2006/0103506 | A1 * | 5/2006 | Rodgers | G06K 19/0701 |
| | | | | 340/5.1 |
| 2007/0016007 | A1 | 1/2007 | Govari et al. | |
| 2009/0030646 | A1 | 1/2009 | Jones et al. | |
| 2009/0256751 | A1 * | 10/2009 | Zeller | E21B 47/0232 |
| | | | | 342/463 |
| 2010/0082280 | A1 | 4/2010 | Schneider | |
| 2011/0085720 | A1 | 4/2011 | Averbuch | |
| 2011/0156957 | A1 * | 6/2011 | Waite | G01S 5/0252 |
| | | | | 342/450 |
| 2011/0275925 | A1 | 11/2011 | Leichner | |
| 2011/0313414 | A1 | 12/2011 | Liu et al. | |
| 2013/0303878 | A1 | 11/2013 | Nevo et al. | |
| 2016/0015323 | A1 | 1/2016 | Tathireddy et al. | |
| 2016/0213430 | A1 | 7/2016 | Mucha | |
| 2016/0278746 | A1 | 9/2016 | Hancu et al. | |
| 2017/0090568 | A1 * | 3/2017 | Chen | G06F 3/014 |
| 2017/0347915 | A1 | 12/2017 | Weprin et al. | |
| 2017/0351094 | A1 * | 12/2017 | Poulos | G02B 27/017 |
| 2018/0110562 | A1 | 4/2018 | Govari et al. | |
| 2018/0193100 | A1 | 7/2018 | Larkin et al. | |
| 2018/0220928 | A1 | 8/2018 | Blood et al. | |
| 2018/0221610 | A1 | 8/2018 | Larson et al. | |
| 2018/0373288 | A1 | 12/2018 | Govari et al. | |
| 2019/0056243 | A1 | 2/2019 | Foster et al. | |
| 2019/0089059 | A1 * | 3/2019 | Pelrine | H01Q 7/06 |
| 2019/0111233 | A1 | 4/2019 | Beeckler et al. | |
| 2022/0175468 | A1 | 6/2022 | Barak et al. | |

FOREIGN PATENT DOCUMENTS

| | | |
|---|---|---|
| WO | WO 2020/129050 | 6/2020 |
| WO | WO 2021/048837 | 3/2021 |

OTHER PUBLICATIONS

Supplementary European Search Report and the European Search Opinion dated Sep. 1, 2022 From the European Patent Office Re. Application No. 20862152.4. (7 Pages).
Strachen et al. "Accurate Indoor Navigation With Spinning Magnets", International Conference on Information Processing in Sensor Networks, IPSN '18, Porto, Portugal, Apr. 11-13, 2018, 2 P., Apr. 11, 2018.
International Preliminary Report on Patentability dated Jul. 1, 2021 From the International Bureau of WIPO Re. Application No. PCT/IL2019/051363. (8 Pages).
International Search Report and the Written Opinion dated Sep. 9, 2019 From the International Searching Authority Re. Application No. PCT/IL2020/050972. (26 Pages).
International Search Report and the Written Opinion dated Feb. 26, 2020 From the International Searching Authority Re. Application No. PCT/IL2019/051363. (11 Pages).
Rotenberg et al. "Compensation of Magnetic Disturbances Improves Inertial and Magnetic Sensing of Human Body Segment Orientation", IEEE Transactions on Neural Systems and Rehabilitation Engineering ,13(3): 395-405, Sep. 12, 2005.
International Preliminary Report on Patentability dated Mar. 17, 2022 From the International Bureau of WIPO Re. Application No. PCT/IL2020/050972. (6 Pages).
Interview Summary dated Aug. 12, 2022 from US Patent and Trademark Office Re. U.S. Appl. No. 17/681,789. (2 pages).
Supplementary European Search Report and the European Search Opinion dated Apr. 21, 2022 From the European Patent Office Re. Application No. 19899014.5. (6 Pages).
Official Action dated May 12, 2022 from US Patent and Trademark Office Re. Application No. 17/681,789. (29 pages).
Notice of Allowance dated Mar. 15, 2023 from the US Patent and Trademark Office Re. U.S. Appl. No. 17/681,789. (12 pages).
Communication Pursuant to Article 94(3) EPC Dated Mar. 25, 2024 From the European Patent Office Re. Application No. 20862152.4. (4 Pages).

* cited by examiner

MAGNETIC LOCALIZATION USING A DC MAGNETOMETER

RELATED APPLICATIONS

This application is a National Phase of PCT Patent Application No. PCT/IL2019/051363 having International filing date of Dec. 12, 2019, which claims the benefit of priority under 35 USC § 119(e) of U.S. Provisional Patent Application Nos. 62/897,599 filed on Sep. 9, 2019 and 62/780,291 filed on Dec. 16, 2018. The contents of the above applications are all incorporated by reference as if fully set forth herein in their entirety.

BACKGROUND

Known Electromagnetic (EM) localization systems are vastly used for three-dimensional (3D) localization applications, for example in medicine, gaming, VR/AR, navigation and many other fields. Compared with optical-based localization systems, EM systems are usually highly power-efficient and do not suffer from optical problems such as occlusions, motion blur, feature tracking failures etc. (although might be subject to other EM specific problems such as distortion due to nearby metals and interference due to nearby EM radiating devices). EM localization systems are especially useful in the Medical field where special tools need to be localized inside the body. In these cases optical-based localization systems are usually irrelevant due to the lack of line of sight.

Some known system may include an EM field sensor/receiver and an EM field generator/transmitter that transmits multiple different alternating ("AC") EM fields, for example sinusoidal EM fields. The receiver usually receives a combination of the multiple EM fields from the transmitter, and differentiates between the different fields, for example by performing a Fast Fourier Transform (FFT) and/or a Discrete Fourier Transform (DFT) or any other suitable method. By analyzing the phases and/or amplitudes, the receiver identifies a unique EM signature associated with a specific position and orientation, e.g. a specific six-degrees-of-freedom (6DOF) state, for example three coordinates of position and three angles of orientation. In other systems the EM signature is used to recover only five-degrees-of-freedom (5DOF). In these systems the roll angle of the sensor is usually absent. In other systems only the position may be solved (3DOF) and the orientation of the sensor remains unknown.

Reference is now made to FIG. 1, which is a schematic illustration of a known EM localization system 900. System 900 may include at least one EM field generator/transmitter 90 that transmits multiple different alternating ("AC") EM fields, for example sinusoidal EM fields, and at least one EM field sensor/receiver 92. Receiver 92 receives a combination of the multiple EM fields from transmitter 90, e.g. a superposition of the transmitted fields. Receiver 92 may include at least one hardware processor 94 and memory 96. Processor 94 may differentiate between the different fields, for example by performing a Fast Fourier Transform (FFT) and/or a Discrete Fourier Transform (DFT) or any other suitable method. Processor 94 may analyse the phases and/or amplitudes to identify a unique EM signature associated with a specific position and orientation, e.g. a specific six-degrees-of-freedom (6DOF) state, for example three coordinates of position and three angles of orientation. Processor 94 may convert the received combination of EM fields to the 6DOF state, for example continuously and/or in real time.

In order to enable decomposition of the received combination of fields and/or distinguishing between the received fields and identification of a unique 6DOF state of the monitored object, transmitter 90 needs to transmit multiple EM sinusoidal field signals in carefully chosen frequencies, for example so that the sinusoidal field signals are orthogonal to each other. Some systems may include N coils which generate according to Ampere's law slightly different EM fields using electrical current. The number N should be large enough to enable identification of the 6DOF state of the monitored object. In other systems, there may be a smaller number of coils that generate orthogonal and/or otherwise highly distinctive EM field signals. For example, an electromagnetic localization system may include three coils that generate three distinct EM field signals, respectively, enabling processor 94 to recognize the three distinct fields and three scalar values per field per location of the monitored object, thus identifying nine values unique for the object's position and orientation. Receiver 92 may usually include three orthogonal receiving coils that sense according to Faraday's law of induction the combination of transmitted fields and generate respective three electromotive force (EMF) voltage signals. In order to enhance the distinction between the fields and amplify the pickups of the fields in the receiver, the system may usually use high-frequency EM fields, in the kHz scale. Processor 94 may then calculate the 6DOF state by assuming a constant position and orientation state within a short-time period, and performing a DFT. This process may repeat continuously and/or may be performed in real time.

Some known every-day devices such as, for example mobile phone devices, include an Inertial Measurement Unit (IMU), that provides information of the device's motion. Usually, the IMU includes digital sensors such as an accelerometer and gyroscope, and in many cases a magnetometer. The accelerometer mainly senses the gravity force vector (plus some local, linear acceleration which can be filtered out using some sensor-fusion methods) and therefore may enable detection of partial orientation, for example of the device's screen (landscape/portrait). The gyroscope senses angular velocity of the device. Since these two sensors have no reference except for the gravity force (which points to the sky), the computed orientation usually drifts slowly around the gravity vector. In this sense, orientation tracking based on accelerometer and gyroscope alone is considered "drifting", since it has no stable reference. In many applications, the data received from the accelerometer and the gyroscope are combined to provide robust orientation tracking of the device. The magnetometer may be used to sense Earth's DC magnetic field, for example using Hall effect sensors, magneto-resistive sensors, magneto-inductive sensors, and/or by any other suitable sensor type. The sensed Earth's DC magnetic field may be used to correct drifting of the accelerometer and gyroscope orientation detection in Earth's coordinates. However, the magnetometer readings are often distorted by various elements in its environment, such as nearby metals (soft-iron, hard-iron distortion). In addition, low-cost magnetometer sensors are prone to bias calibration problems, where the internal bias of the sensor drifts over time. Therefore, many applications choose to ignore the magnetometer data and detect orientation by the accelerometer and gyroscope only, although the identified orientation usually drifts over time with respect to Earth's North, since the magnetometer data is dismissed and no other sensor is used for additional orientation reference.

SUMMARY

An aspect of some embodiments of the present invention provides a magnetic localization system comprising: a magnetic field generator configured to generate an alternating magnetic field with a maintained frequency; and a receiver comprising: a DC magnetometer to sense a local magnetic field, at least in part due to the generated magnetic field; and at least one processor configured to calculate a six-degrees-of-freedom (6DOF) position and orientation of the receiver relative to the generator, based on the sensed magnetic field and the maintained frequency.

Optionally, the generator is configured to communicate a momentary phase of the generated field, and wherein the at least one processor further calculates the position and orientation based on the momentary phase.

Optionally, the receiver and/or generator comprises a sensor bundle to sense and/or compute acceleration and/or orientation values of the receiver and/or generator, respectively, and wherein the at least one processor is configured to calculate the 6DOF position and orientation further based on the sensed and/or computed acceleration and/or orientation values.

Optionally, the at least one processor is configured to calculate the 6DOF position and orientation by: extracting from the sensed magnetic field the local magnetic fields that are due to magnetic field components in at least two orthogonal directions of the generated magnetic field as generated by the generator; and finding the position and/or orientation of the receiver by finding a unique solution for these extracted magnetic fields.

Optionally, the magnetic field generator comprises: an actuator configured to apply a rotational motion; at least one magnet rotating about a first axis by the actuator; a magnetometer to sense a momentary rotation phase of the at least one magnet; and a controller to maintain a desired rotation frequency of the at least one magnet.

Optionally, the generator and the receiver share a clock reading between them.

Optionally, the generator is configured to communicate a timestamp together with the maintained rotation frequency and the sensed momentary phase.

Optionally, the sensed and/or computed acceleration and/or orientation values includes a gravity vector, a linear acceleration and/or orientation of the receiver and/or generator.

Optionally, the generator includes a processing unit for tracking the phase of the at least one rotating magnet.

Optionally, the receiver and/or generator includes a processing unit for fusion of a sensor bundle, for phase tracking, and/or for computation of 6DOF position and orientation of the receiver relative to the generator.

Optionally, the generator is configured to: sense by the generator's magnetometer a magnetic field generated by the cyclic motion of the at least one rotating magnet; calculate parameters of the sensed rotating magnetic field; and extract a momentary phase of the cyclic motion of the at least one rotating magnet based on the calculated parameters.

Optionally, the at least one processor is configured to predict a next value of the momentary phase of the at least one rotating magnet, by: sampling receiver clock timestamps upon receiving a transmitter clock timestamp and identifying a linear relation between the receiver clock and the transmitter clock; and converting a receiver clock value to a transmitter clock value based on the identified relation; and use the computed time difference in transmitter clock to extrapolate the phase.

Optionally, the actuator comprises: at least two electromagnets to cause a rotational motion of the at least one magnet by their applied torque; and a microcontroller to control electromagnetic fields produced by the at least two electromagnets for regulated rotation.

Optionally, the actuator comprises at least one of a list consisting of a DC motor (for example, brushed or brushless), fluid driven rotation mechanism, air turbine, hydraulic motor, a combustion engine and a steam engine.

Optionally, the at least one magnet is further rotated about a second axis and the generator senses by the magnetometer the corresponding generated magnetic fields and accordingly calculates momentary phases of the at least one magnet, in the rotational motions about the first axis and about the second axis.

Optionally, the cyclic motion about the first and second axes is produced by mounting the at least one magnet and/or motor on a camshaft of a second motor.

Optionally, the cyclic motion about the first and second axes is applied to the at least one magnet by mounting the at least one magnet on a shaft, the shaft is free to rotate and move axially and includes a radial pin mechanically connected to a groove in a surrounding sleeve.

Optionally, the groove is in the shaft and the pin is stationary.

Optionally, the receiver detects low-frequency position and orientation data by a magnetometer and high-frequency position and orientation data by a gyroscope and/or accelerometer.

Optionally, the at least one processor uses a Kalman filter, in which a magnetic localization provides readings for position and orientation, and an accelerometer and/or a gyroscope provide readings for linear acceleration and/or a gyroscope provides readings for angular velocities.

BRIEF DESCRIPTION OF THE DRAWINGS

Some non-limiting exemplary embodiments or features of the disclosed subject matter are illustrated in the following drawings.

In the Drawings.

Figure 1:
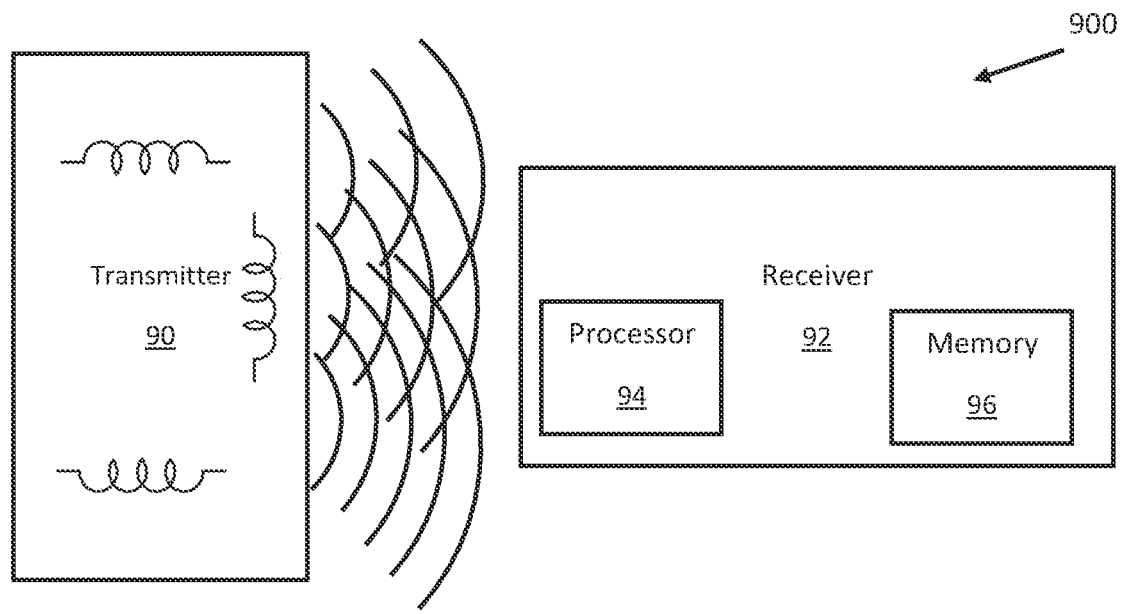
FIG. 1 is a schematic illustration of a known EM localization system.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present invention provide a localization method and system compatible with standard and/or low-cost receiver sensors, such as a standard IMU or any other suitable sensor bundle. The provided system includes a new and inventive transmitter design, which allows for a bundle of standard and/or low-cost sensors, for example any suitable configuration and/or combination of a magnetometer, a gyroscope, an accelerometer, and/or any other suitable sensors, to serve as a fully functional sensor/receiver operating at a real-time rate, by sophisticated algorithmic processing.

A magnetometer, as referred to throughout the present description, usually operates at a sampling rate of an order of magnitude of hundreds of Hz, for example of about 100 Hz and/or up to 500 Hz-1000 Hz. In order to use a direct-current (DC) magnetometer (one that measures DC magnetic fields) as an alternate-current (AC) magnetic sensor (one that is intended for use with AC magnetic fields), the sensed AC magnetic field must be of a frequency significantly smaller than the magnetometer's sampling rate, e.g. an order of magnitude smaller. The sensed magnetic fields should be in a range detectable by the DC magnetometer. For example, the sensed magnetic field should be about ten times the magnetometer's sensitivity when generated, and take into account also the noise level, in order to be detected by the magnetometer. For example, a DC magnetometer can detect magnetic fields of between a few µT to a few thousands of µT (For example, between 1 to 4000 µT) with sensitivity, e.g. resolution, of about 0.1 µT. Since a magnetic field's strength is inversely proportional to the cube of the distance between the dipole source and the receiver, the sensing range should have a factor ~10 between the minimal to the maximal distances, for example 10 cm to 1 m or 1 m to 10 m, etc.

For all the reasons mentioned above, traditional EM systems are comprised of a specially designed transmitter for transmitting AC EM fields at carefully chosen frequencies, for example in the order of magnitude of kHz, as well as a corresponding receiver design, built to sense those fields relying on Faraday's law of induction, with special receiving coils connected to unique filters and amplifiers and analog-to-digital units, operating at high enough speeds to allow for very dense sampling of the fields' AC periods, fast enough to support for a successful DFT. This makes standard sensors, such as standard DC magnetometers, unsuitable for use as receivers in traditional EM localization systems.

In contrast, localization systems provided according to some embodiments of the present invention include a transmitter design combined with a processing method that enables, for example, a standard IMU to serve as a fully functional tracked EM receiver, which may operate at a real-time rate, according to some embodiments.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

Figure 2:
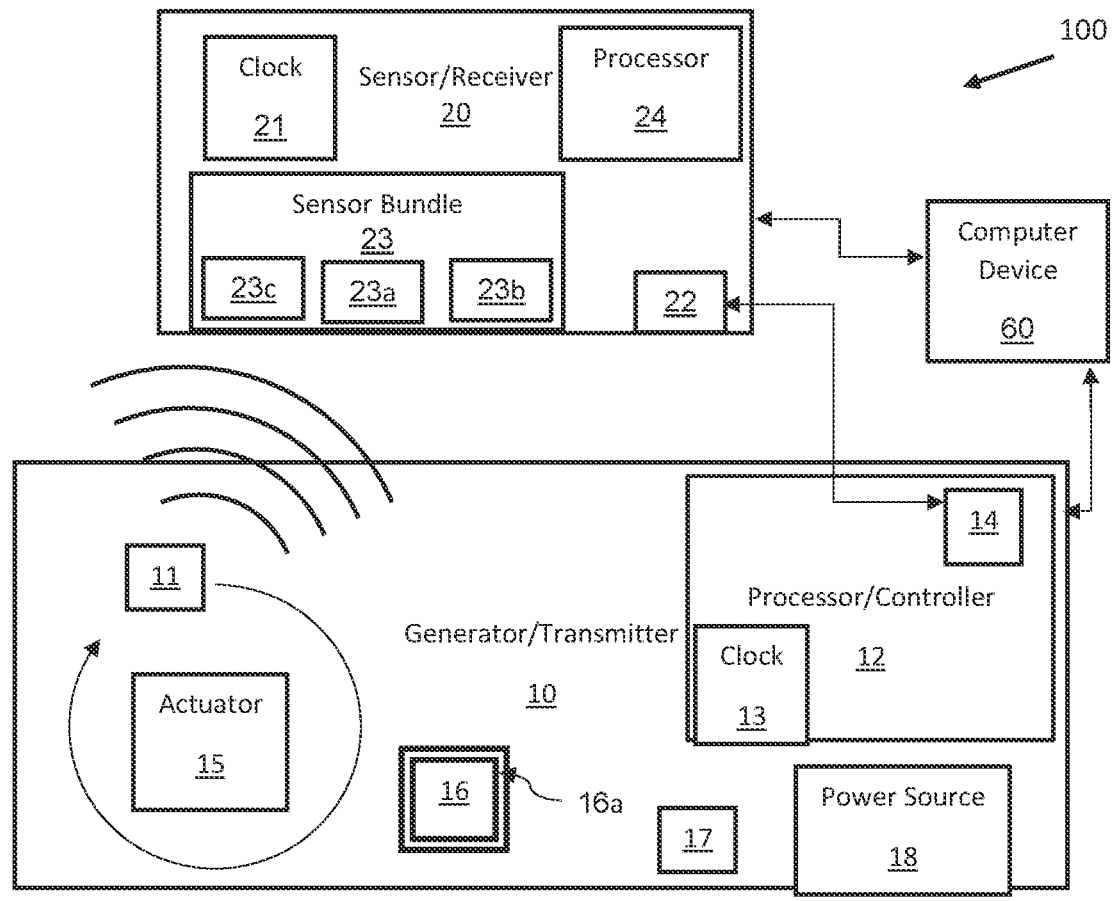
FIG. 2 is a schematic illustration of a system for magnetic localization using an inertial measurement unit, according to some embodiments of the present invention.

Reference is now made to FIG. 2, which is a schematic illustration of a system 100 for magnetic localization using an inertial measurement unit, according to some embodiments of the present invention. System 100 includes a generator/transmitter 10 and an electromagnetic sensor/receiver 20. Generator/transmitter 10 may be configured to generate an alternating (AC) magnetic field with a maintained frequency. Generator/transmitter 10 may further be configured to communicate to receiver 20 the maintained frequency and/or a momentary phase of the generated field.

Figure 3:
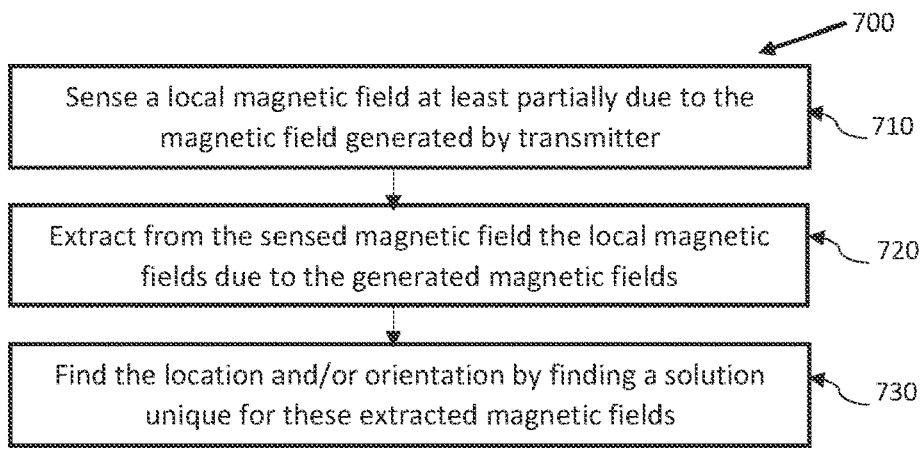
FIG. 3 is a schematic flowchart illustrating a method for calculating a 6DOF location and orientation of the sensor/receiver relative to transmitter, according to some embodiments of the present invention.

Reference is further made to FIG. 3, which is a schematic flowchart illustrating a method 700 for calculating a 6DOF location and orientation of the sensor/receiver 20 relative to transmitter 10, according to some embodiments of the present invention. Sensor/receiver 20 is configured to calculate a 6DOF location and orientation of the sensor/receiver 20 relative to transmitter 10, for example based on the frequency and, in some embodiments, momentary phase received from the generator, for example as described in more detail herein below and/or throughout the present description. For example, as indicated in block 710, receiver 20 may sense a local magnetic field at least partially due to the magnetic field generated by transmitter 10. As indicated in block 720, receiver 20 may extract from the sensed general magnetic field the local magnetic fields that are due to the generated magnetic field components in at least two orthogonal directions as generated by transmitter 10. As indicated in block 730, receiver 20 may find the location and/or orientation of the receiver by finding a unique solution for these extracted magnetic fields, for example by solving magnetic dipole equations for these extracted fields and/or by Kalman filter or non-linear optimization methods as described in more detail herein. In some embodiments, receiver 20 may utilize DFT methods for finding the solution.

In some embodiments of the present invention, generator/transmitter 10 may include at least one permanent magnet 11, a processor/controller 12 having an inner clock 13 and a communication interface 14, an actuator device 15, a strong-field magnetometer 16, possibly having a magnetic shield 16a, a sensor bundle 17, for example an IMU, and a power source 18. Actuator device 15 may be configured to apply a rotational motion on magnet 11.

In some embodiments, generator/transmitter 10 generates a low-frequency electromagnetic field of, for example, less than 30 Hz, having strength of, for example, about 1 µT or stronger at, for example, about 1 meter from the transmitter. Usually, in order to produce such a strong field by an AC electric current according to Ampere's law, a very large transmitter with very high-power consumption is required.

However, according to some embodiments of the present invention, generator/transmitter 10 includes at least one permanent magnet 11 that generates the magnetic field. By producing the magnetic field by at least one permanent magnet, the magnetic field produced by generator/transmitter 10 may be about a hundred times stronger than a magnetic field produced by AC electric current, by a transmitter of similar dimensions, and results in an extremely low-power transmitter. The material of the magnet is chosen to maximize the generated magnetic field strength compared to the size of generator/transmitter 10. For example, generator/transmitter 10 may include a rare-Earth magnet, for example a Neodymium magnet or magnet of another suitable material.

In order to produce an AC magnetic field, in some embodiments of the present invention, magnet 11 is mounted on an axis rotated, for example, by an actuator 15, for example a direct-current (DC) motor, or by electromagnetic coils around magnet 11 which produce a weak AC field, strong enough to rotate the magnet at their center by the applied torque, as described in more detail below, or any other suitable device, at a desired operating frequency f Thus, for example, rotating magnet 11 results in an AC magnetic field in the surrounding space. The magnetic field generated by the rotating magnet 11 may be expressed as the superposition of two AC magnetic field of frequency f and orthogonal phases and generated by two separate virtual EM coils x and y:

$$B(\vec{r},t)=B_x(\vec{r})\cos(\varphi(t))+B_y(\vec{r})\sin(\varphi(t))$$

where φ(t) is the momentary phase within the rotation of the rotating magnet 11. In a perfect setting φ(t)=ωt, that is, the transmitter produces perfectly fixed frequency ω=2πf, but in more practical scenarios this is just an approximation which can be expressed as: $\dot{\varphi}(t) \approx \omega$. $B_x$ is the magnetic dipole field due to the 'x' virtual coil and $B_y$ is the magnetic dipole field due to the 'y' virtual coil. In other words, $B_x$, $B_y$ are two magnetic fields corresponding to virtual 'x' and 'y' axes of the rotating magnet 11, respectively. It will be appreciated that according to some embodiments of the present invention, magnet 11 may be controlled to move according to other, for example more complicated, motion models. For example, magnet 11 may be rotated about a time-varying axis direction. For example, the movement of magnet 11 may include a combination of rotational motion about a fixed axis and a periodic linear motion parallel to the fixed axis. Other motion models are also in the scope of the present invention. In some embodiments, the more complicated motion models may add an additional orthogonal virtual coil 'z' whose dipole field is denoted $B_z(\vec{r})$ and that may enhance the position and orientation calculations. This is while keeping the ability of magnetometer 16 to detect the momentary position, e.g. phases, of magnet 11.

In some embodiments, magnet 11 may be controlled by generator 10 to rotate about an additional, secondary, axis, to obtain a more complex magnetic field sensed by receiver 20 and thus, for example, provide more information for the position and orientation calculation. Magnetometer 16 may sense the corresponding generated magnetic fields and accordingly calculate momentary phases of magnet 11, in the rotational motions about the first axis and the secondary axis, and transmit the calculated momentary phases to receiver 20. For example, as shown with reference to FIG. 7, described in more detail herein below, the cyclic motion of magnet 11 is produced by mounting magnet 11 and/or a first motor on a camshaft of a second motor. For example, the cyclic motion about the first and second axes is applied to magnet 11 by mounting magnet 11 on a shaft, the shaft is free to rotate and move axially and includes a radial pin engaged in a groove in a surrounding sleeve. Optionally, the groove is in the shaft and the pin extends from the sleeve radially into the groove.

Processor/controller 12, for example a microprocessor/controller, may maintain a permanent desired frequency f of the generated magnetic field, for example the frequency in which actuator 15 operates and/or magnet 11 rotates. For example, a desired frequency f is inherent to and/or embedded in the hardware of controller 12 and/or transmitter 10. For example, actuator 15 may be a highly stable motor and/or or a specially designed motor, for example, operating according to a clock 13 of controller 12, or otherwise maintaining a substantially constant frequency. In some embodiments, controller 12 may switch between various possible frequencies to maintain, for example by maintaining corresponding voltage levels provided to actuator 15, in a closed feedback loop with the transmitter's magnetometer 16 (serving as a rotary sensor), causing transmitter 10 to generate AC field in a desired maintained frequency f. In some embodiments, controller 12 may include hardware and/or software components to change the frequency f. The maintained frequency f may be communicated to receiver/sensor 20, for example by controller 12, for example by communication interface 14. Communication interface 14 may include a low-power radio transmitter/receiver, for example a 2.4 GHz transmitter/receiver, and/or a Low-Energy Bluetooth device, a WiFi communication device, a USB cable, or any other suitable communication device. Receiver/sensor 20 may include an inner clock 21 and may include a corresponding communication device 22 to receive communication from processor/controller 12. In some embodiments, receiver 20 and generator/transmitter 10 share a clock, for example, by using a single oscillator wired to both devices, or by using two separate oscillators and a sync wire, aligning the clock readings of both devices periodically. Receiver/sensor 20 may also use its communication device 22 to transmit computed 6DOF states to a host computer device 60, such as a PC, a gaming console and/or any other suitable computer device that may host an application using data received from receiver 20. For example, computer device 60 may receive the 6DOF position states from receiver 20, for example in real time, and/or may receive raw sensor readings from receiver 20 and/or generator 10 and perform 6DOF calculations, and/or may display and/or otherwise use a corresponding moving object on a screen or as a video game object and/or a cursor or controller for selection and/or control of an object and/or a trackable object inside the body, for example during medical procedure. Further, receiver/sensor 20 may include a sensor bundle 23 including a magnetometer 23a, and in some embodiments gyroscope 23b and/or accelerometer 23c, and a processor 24 to calculate the position of receiver 20 relative to transmitter 10, e.g. the position of receiver 20 in a coordinate system centered at transmitter 10, for example including location and orientation, for example using 6DOF representation. Magnetometer 23a may be configured to sense magnetic field generated by generator/transmitter 10. Sensor bundle 23 may include an IMU that may include gyroscope 23b and accelerometer 23c, and in some embodiments the IMU may include magnetometer 23a.

In some embodiments of the present invention, processor 24 is separate from receiver 20 and/or at least some of the operations and/or calculations described herein with reference to receiver 20 or processor 24 may be performed by at least one processor separate from receiver 20, for example a processor communicating with receiver 20 and/or transmitter 10. For example, at least some of the calculations and/or operations may be performed by a host computer device 60.

According to some embodiments of the present invention, transmitter 10 may include a magnetometer 16, located at a fixed location relative to rotating magnet 11. For example, magnetometer 16 or any other suitable magnetometer may be installed in transmitter 10. Magnetometer 16 may sense the rotation periods of magnet 11 and where in the period magnet 11 is located, e.g. the rotation momentary phase φ(t) of magnet 11. As indicated in more detail herein, the rotation phase of magnet 11 may include one or two rotation phases about corresponding one or two axes. For example, magnetometer 16 may provide an estimation of the phase of magnet 11, for example by principle component analysis (PCA) of magnetic samples collected over many rotation periods, for example to extract the axes of an ellipse drawn in a local magnetometer coordinate system centered at transmitter 10 by rotating magnet 11, or any other suitable method for detecting the phase of magnet 11. As the rotation frequency of the magnet 11 is significantly lower relative to the sampling rate of magnetometer 16, e.g. a sampling rate in the range of about 100 Hz-1000 Hz, the rotation phase of magnet 11 can be estimated more accurately. Therefore, in some embodiments of the present invention, the rotation frequency of magnet 11 is much lower than the sampling rate of magnetometer 16, for example an order of magnitude lower, for example up to about 10 Hz-100 Hz, according to the sampling rate of magnetometer 16. Accordingly, processor/controller 12 may calculate the rotation phase of magnet 11 and/or communicate the calculated phase to receiver 20, for example by interface 14. Magnetometer 16 may, in some embodiments, be included in sensor bundle 17, for example an IMU sensor. In other embodiments, magnetometer 16 may be a strong-field magnetometer sensor, separate from sensor bundle 17, whereas sensor bundle 17 may consist of an accelerometer and/or gyroscope only.

The generated magnetic field generated by magnet 11 may be too strong in the location of magnetometer 16, for example because of the proximity of magnetometer 16 to magnet 11. For example, the magnetic field in the location of magnetometer 16 may be stronger than about 4000 μT, which may bring magnetometer 16 into saturation where the actual strong magnetic field is not accurately sensed. In order to solve this problem, transmitter 10 may include a magnetic shield 16a for reducing the magnetic field sensed by magnetometer 16, for example a metal shield such as a metal plate, that may induce some local magnetic distortion, thus, for example, reducing the magnetic field at the location of magnetometer 16, while still enabling to estimate accurately the rotation phase from the distorted magnetic field due to the linear nature of magnetic distortions. Alternatively, magnetometer 16 can be a strong-field magnetometer, designed to sense strong magnetic fields, in the range of up to 100 mT, eliminating the need for a special magnetic shielding.

As described in detail herein, unlike traditional electromagnetic transmitter units, such as transmitter 90 shown in FIG. 1, transmitter 10 may not generate any electric current for creating the magnetic fields. Transmitter 10 utilizes, in some embodiments, the already existing field generated by permanent magnet 11. Therefore, the power consumption of transmitter 10 may be much lower compared to traditional transmitter 90, which may allow it to operate, for example, tens of hours on a few standard batteries. Thus, for example power source 18 providing power to transmitter 10 may be a low-power source such as disposable and/or rechargeable batteries and/or any other suitable low-power source. Rotating the magnet either using a standard DC motor or by weak AC fields produced by coils at the proximity of the magnet, which apply torque on the magnet and cause it to rotate, consumes much less power than generating the same AC field using a standard EM transmitter.

Figure 4:
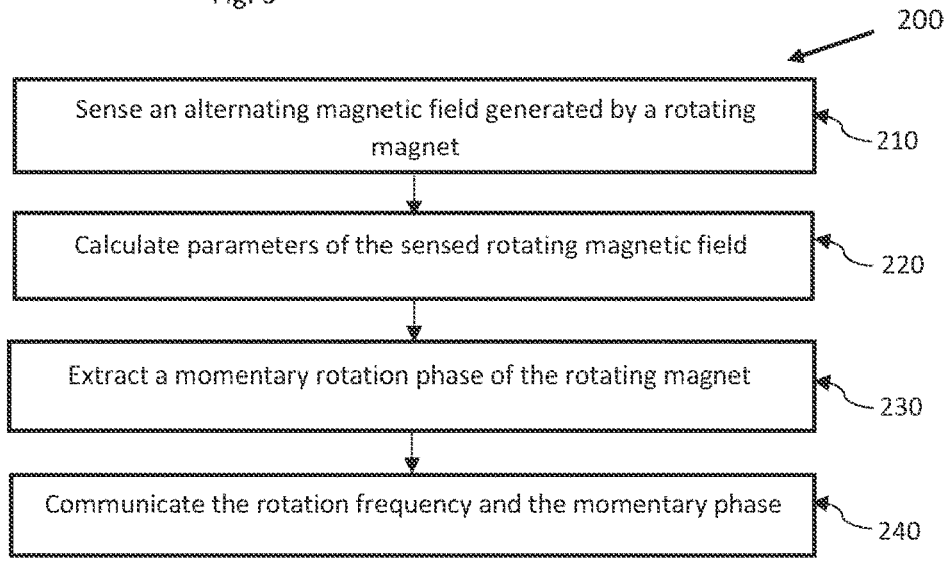
FIG. 4 is a schematic flowchart illustrating a method for estimation of the cyclic motion phase of a magnet, according to some embodiments of the present invention.

Reference is now made to FIG. 4, which is a schematic flowchart illustrating a method 200 for estimation of the rotation phase of magnet 11, for example by processor/controller 12 as discussed herein, according to some embodiments of the present invention. As indicated in block 210, magnetometer 16, located at a fixed position relative to rotating magnet 11, may sense the alternating magnetic field generated by rotating magnet 11. As indicated in block 220, processor/controller 12 may calculate parameters of the alternating magnetic field based on the magnetic field sensed by magnetometer 16, for example, according to the formula:

$$M(t)=M_0+B_x \cos(\varphi(t))+B_y \sin(\varphi(t))$$

wherein φ(t) is the momentary phase of the alternating magnetic field, for example of the rotation of the rotating magnet 11, $B_x$, $B_y$ are the two magnetic fields corresponding to the virtual 'x' and 'y' axes of the rotating magnet 11, respectively, e.g. the magnetic field components in two orthogonal directions as generated at transmitter 10 and/or sensed by magnetometer 16, in local coordinates of magnetometer 16. For example, $B_x$, $B_y$ are the magnetic field components sensed in local coordinates of magnetometer 16 when the rotating magnet points towards 'x' and 'y' axes of the generator's coordinates, respectively, whereas any in between rotation phase can be described using superposition as in the formula above. $M_0$ is the magnetic bias which comprises of intrinsic magnetometer sensor bias (which may slowly drift over time) and of environmental magnetic field at the position of magnetometer 16 (mostly Earth's DC magnetic field). We note that the alternating magnetic field $M(t) \in R^3$ is a periodic function in t with a time period of 1/f. More specifically, M(t) describes an ellipse embedded in $R^3$ whose axes relate to $B_x$, $B_y$. Processor 10 may, for example, take a measurements window of a few seconds and/or reconstruct the ellipse (for example, using simple PCA methods or any other suitable methods) and/or find parameters of the alternating magnetic field such as $M_0$, $B_x$, $B_y$ in any suitable known method. As indicated in block 230, based on the calculated parameters of the generated alternating field M(t), processor 12 may calculate a momentary rotation phase of magnet 11, φ, for example by inverting M(φ) according to the calculated parameters, such as $M_0$, $B_x$, $B_y$. Thus, for example, processor 12 may assign a very accurate phase angle φ for any M(t) measured by magnetometer 16, for example at a real-time rate, for example of about 100 Hz or according to the sampling rate of magnetometer 16. In some embodiments, a Kalman filter is used for identifying the parameters of the alternating magnetic field and/or extracting the momentary phase angle φ and/or angular velocity ω. In some embodiments of the present invention, other motion models of magnet 11 and/or equations for M(t) are applicable, wherein the parameters of the motion and/or of the resulting magnetic field may be extracted by the transmitter's magnetometer 16 and may be communicated to receiver 20 and/or computer device 60.

Therefore, some embodiments of the present invention provide a magnetic field generator/transmitter structure that may calculate a very accurate phase angle of rotating magnet 11, with a reliable and simple structure, low power consumption and without complicated and/or cumbersome mechanical structures. The provided transmitter 10 structure enables real-time calculation of the rotation phase V, for example at the sampling rate of magnetometer 16, for example by rotating magnet 11 at a significantly lower rate, for example controlled by inner clock 13 as discussed herein.

As indicated in block 240, transmitter 10 may communicate to receiver 20 and/or computer device 60 the values of the maintained rotation frequency and the momentary calculated rotation phase V, thus, for example, sensor/receiver 20 and/or compute device 60 may calculate the location and orientation, for example with 6DOF representation, of receiver 20 relative to transmitter 10, for example based on phase V and the rotation frequency.

In some embodiments of the present invention, the phase and/or rotation frequency of magnet 11 may not be transmitted to receiver 20 and/or computer device 60 by transmitter 10. According to some embodiments of the present invention, transmitter 10 may rotate magnet 11 in a unique non-uniform motion profile, enabling receiver 20 and/or computer device 60 to identify the momentary phase according to a known pre-defined motion profile and/or periodical data received from transmitter 10. For example, transmitter 10 may cause magnet 11 to move in a periodic non-uniform motion profile, for example by a stepper motor or any other suitable motor, producing non-constant, non-uniform motion. Receiver 20 may sense by magnetometer 23a the magnetic field generated by the non-uniform motion of magnet 11 and extract/calculate the momentary phase of the magnet by matching momentary sensed magnetic field with the predefined motion profile. For example, the non-uniform motion may include vibration of magnet 11 caused, for example, by controller 12, for example in the beginning of each period of motion of magnet 11. The vibration may be detected by receiver 20 that has information about the motion profile of magnet 11 and may calculate, for example, a momentary phase of magnet 11 based on the time passed since the last detected vibration. In some embodiments, the momentary phase of magnet 11 may be obtained by other methods such as, for example, by rotary encoders, optical solutions and the like.

In some embodiments of the present invention, the maximal working distance (between receiver 20 and generator 10) may be extended, for example without impacting the minimal distance, by using more than one magnetometer 23a for a multi-gain configuration: For example, utilizing a magnetometer that can sense weak magnetic fields in large distances, where a second magnetometer can be used in distances where the magnetic field is strong and the first magnetometer saturates and provides unreliable measurements. Alternatively, magnetometer 16 can output high dynamic range and/or have controllable different operating gains to support a wide range of magnetic fields and thus increase the effective localization range. The utilization of multiple magnetometers may have additional advantages when their relative positions and orientations are known and fixed. For example, measurements from multiple magnetometers may provide richer data which can yield a more robust output when it is used to calculate 6DOF state of a receiver.

Figure 5:
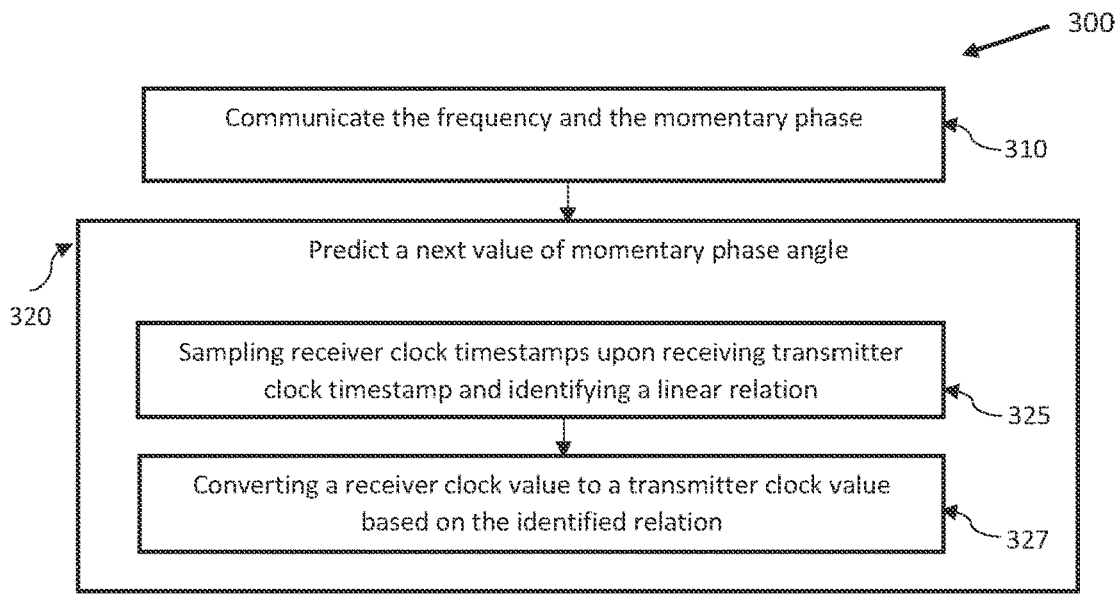
FIG. 5 is a schematic illustration of a method for communication of a cyclic motion phase between a transmitter and a receiver, according to some embodiments of the present invention.

Reference is now made to FIG. 5, which is a schematic illustration of a method 300 for communication between transmitter 10 and receiver 20, according to some embodiments of the present invention. In some embodiments of the present invention, it is important to communicate to sensor/receiver 20 and/or to computer device 60 the momentary phase of magnet 11 corresponding to the magnetic field sensed by sensor 20 in as accurate manner as possible and in real time. For example, for each value of magnetic field sensed by sensor 20, the corresponding momentary phase of magnet 11 must be also known in real-time manner in order to calculate the 6DOF position and orientation of receiver 20 in real time.

In some cases, however, synchronizing between accurate real-time phase of magnet 11 and sensor/receiver 20 is not trivial due to inevitable communication latency between transmitter 10 and receiver 20 and/or computer device 60, especially in a wireless setting. Additionally, with wireless communication random stalls may also occur; data meant to be sent from transmitter 10 and receiver 20 and/or computer device 60 may get stalled either in communication interface 14 or receiver 20, or may be completely dropped due to communication errors. In order to overcome these problems, some embodiments of the present invention provide a method to calculate a predicted phase angle for cases when the real-time rotation phase of magnet 11 is not received or not received fast enough from transmitter 10.

Accordingly, as indicated in block 310, transmitter 10 may communicate to receiver 20 and/or computer device 60 momentary phase angle φ and angular velocity ω, for example as described in detail herein. The communication may be performed, for example, in the rate of detecting the magnetic field by magnetometer 16, herein also referred to as "full rate". In some embodiments, together with phase angle φ and angular velocity ω, transmitter 10 may communicate to receiver 20 and/or computer device 60 a timestamp of clock 13. For example, transmitter 10 may transmit to receiver 20 and/or computer device 60 data packets, each including the timestamp, the momentary phase angle φ and angular velocity ω, for example in full rate.

As indicated in block 320, based on the timestamp, the momentary phase angle φ and angular velocity ω, receiver 20 and/or computer device 60 predicts a next value or next values of momentary phase angle φ, corresponding to the next sensed value or values of magnetic field, respectively. For example, processor 24 calculates the next value or values of momentary phase angle φ by linear extrapolation according to the formula:

$$\varphi(t)=\varphi_0+\omega_0(t-t_0)$$

where $t_0$, $\varphi_0$, $\omega_0$ are the timestamp, momentary phase, and angular velocity, respectively, received, for example, in a data packet, from transmitter 10, and t is the timestamp corresponding to the calculated next value of phase angle φ(t).

However, $t_0$ is a timestamp measured in clock 13, which may be inaccessible for receiver 20. Receiver 20 may be able to measure and/or express timestamps according to the time of clock 21 only. In order to solve this problem, as indicated in block 327, processor 24 may convert between the time of clock 21 and the time of clock 13. For example, in some embodiments of the present invention, processor 24 may identify the linear relation between clock 13 and clock 21. For example, processor 24 may use a Kalman filter to learn the linear relation between clock 13 and clock 21, for example based on (possibly noisy) measurements of the time $t_{tx}$ of the transmitter clock 13 and the time $t_{rx}$ of the receiver clock 21. For example, as indicated in block 325, upon receiving a timestamp $t_{tx}$ of clock 13 from transmitter 10, receiver 20 samples $t_{rx}$ from clock 21 and constructs a pair $(t_{tx}, t_{rx})$, this pair is fed to the clock-synchronization Kalman filter of processor 24. In order to have a timestamp t corresponding to the calculated next value of phase angle φ(t), processor 24 may sample a timestamp $t_{rx}$ from clock 21, convert $t_{rx}$ to $t_{tx}$ by the identified linear relation. Then, receiver 20 may predict a next phase value $\varphi(t_{tx})=\varphi_0+\omega_0(t_{tx}-t_0)$, based on the $t_0$, $\varphi_0$ and $\omega_0$ lastly received from transmitter 10. Thus, for example, receiver 20 may assign a very accurate phase angle to each magnetic field measurement of receiver 20 when phase data from transmitter 10 is delayed, relying on a known motion pattern of the magnet which permits accurate extrapolation of the phase over short periods of time. The above described clock synchronization may alternatively be done by computer device 60 in a same manner, by identifying the relation between timestamp pairs received transmitter 10 and receiver 20, as described above. Clock synchronization may be achieved by other ways as well, for example, by repeatedly exchanging receiver's clock with transmitter's clock using communication in order to eventually compute a linear relation (including latency bias) between receiver and transmitter, by syncing both clocks using a wire or fast RF communication or even by directly wiring the same clock oscillator between transmitter and receiver. As mentioned above, in some embodiments, transmitter 10 shares a clock with receiver 20, for example by using a single oscillator wired to both devices, or by using two separate oscillators and a sync wire, aligning the clock readings of both devices periodically.

Figure 6:
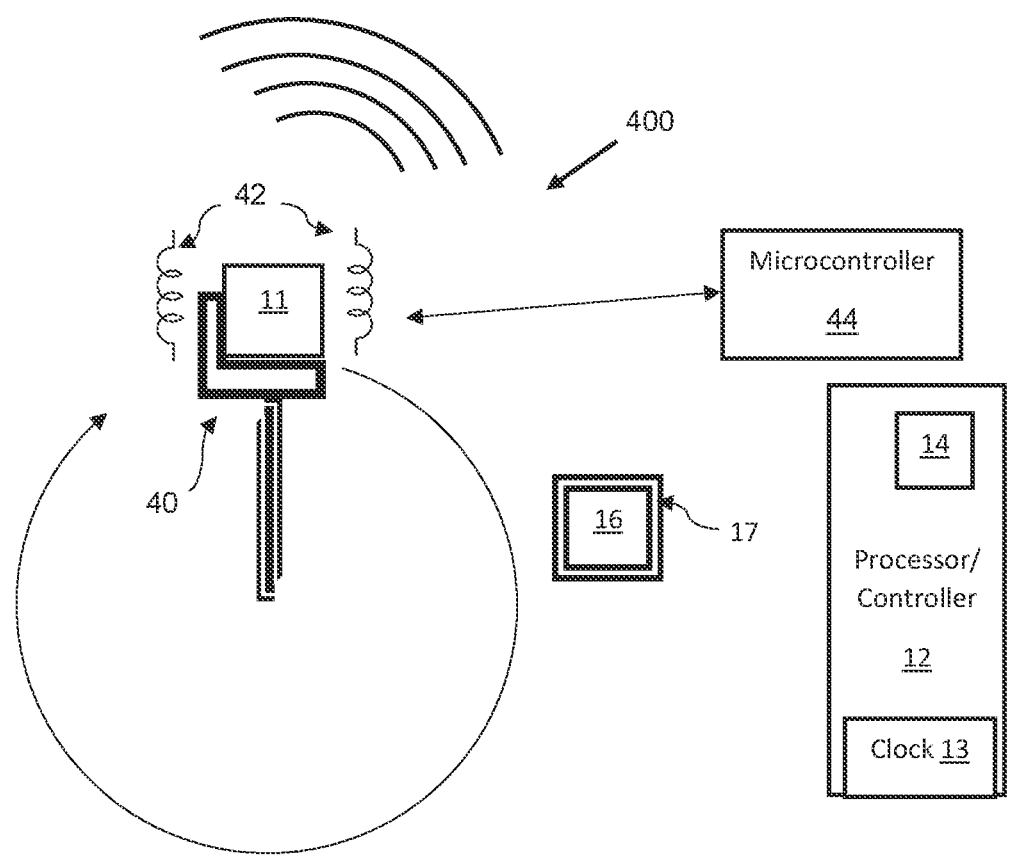
FIG. 6 is a schematic illustration of a motor structure, according to some embodiments of the present invention.

Some embodiments of the present invention provide a special motor structure that may be included in actuator device 15. Reference is now made to FIG. 6, which is a schematic illustration of a motor structure 400, according to some embodiments of the present invention. Motor structure 400 may include rotating permanent magnet 11 mentioned above, utilized for producing the rotational motion of itself. Motor structure 400 may further include two or more electromagnets such as electromagnetic coils 42 wound around magnet 11, or optionally off-the-shelf electromagnetic single-axis coils positioned near magnet 11, which generate weak AC magnetic fields, just sufficiently strong to cause the rotational motion of magnet 11 with their applied torque, and a microcontroller 44, which may or may not be included in controller 12. Microcontroller 44 may switch between coils 42 in order to maintain the rotation and may use magnetometer 16 as a feedback for monitoring and/or regulating the rotational motion of magnet 11. Magnet 11 may be held by a mounting structure 40 that holds magnet 11 and keeps it in its rotational orbit. In some embodiments, mounting structure 40 may include a rotating axis and magnet 11 may be fixed on the rotating axis and/or rotate about the axis. Surrounding coils 42 may be wounded around magnet 11 and the rotating axis.

In such embodiments, the generator's magnet 11 may be bound to rotate at a fixed rate dictated by the weak magnetic fields produced by the surrounding coils 42. These fields may operate at a constant frequency generated by microcontroller 44, causing magnet 11 to rotate at a highly predictable manner according to the microcontroller's internal clock 13. Microcontroller 44 may use feedback information from magnetometer 16 for regulating and/or maintaining the fixed rotation rate. Receiver 20 may deduce the momentary phase of magnet 11 by synchronizing its clock 21 with transmitter's clock 13, relying on a constant rotation rate reported by the transmitter, and may receive updated phase information from transmitter 10 at least occasionally, in order to maintain the phase information sufficiently accurate.

It will be appreciated that in some embodiments, actuator 15, configured to apply a rotational motion on magnet 11, may include at least one of a list consisting of a DC motor (for example, brushed or brushless), a fluid driven rotation mechanism, air turbine, hydraulic motor, a combustion engine and a steam engine.

Figure 7:
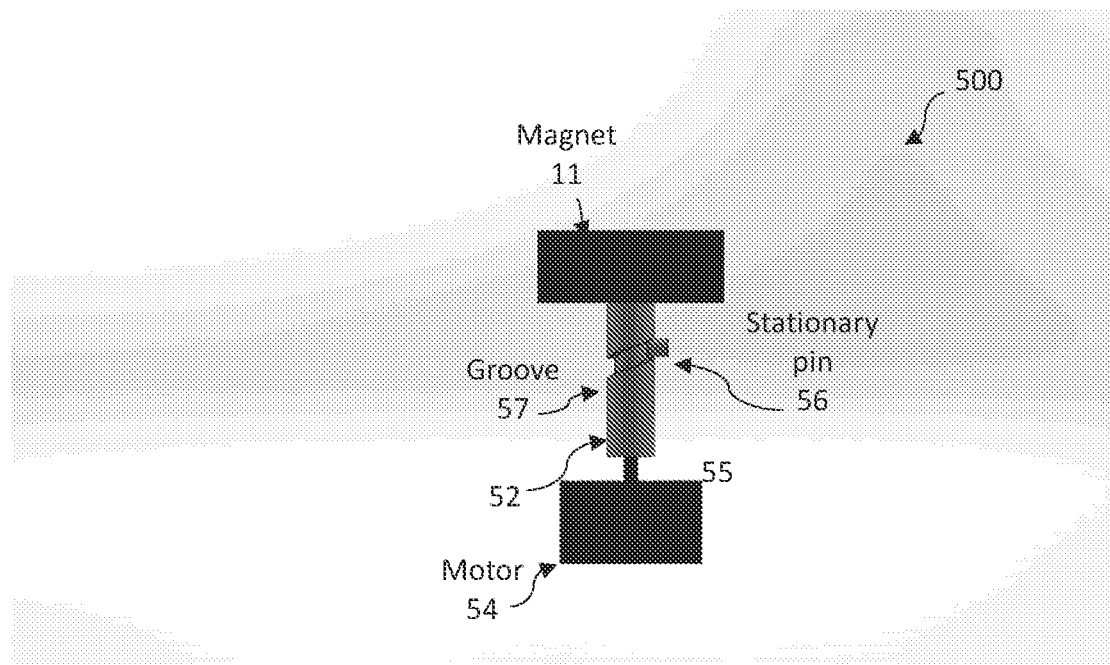
FIG. 7 is a schematic illustration of a motor and shaft structure, allowing a complex cyclic motion, according to some embodiments of the present invention.

Reference is now made to FIG. 7, which is a schematic illustration of an exemplary motor structure 500, according to some embodiments of the present invention. Motor structure 500 may include motor 54 and a magnet 11 attached to a sleeve 52, wherein sleeve 52 may be mounted on a camshaft 55 of motor 54. In some embodiments, magnet 11 may be controlled by generator 10 to rotate with sleeve 52 about camshaft 55. Motor 54 may cause shaft 55 to rotate and/or move axially in sleeve 52. Shaft 55 may have a pin 56 that engages to a groove 57 in the surrounding sleeve 52. Pin 56 may extend radially from shaft 55 and may move in a groove 57 when shaft 55 rotates and/or moves axially. Groove 57 may have a spiral shape so that, for example, an axial motion of shaft 55 relative to sleeve 52 causes an additional rotational motion of shaft 55 relative to sleeve 52, and vice-versa. Optionally, the groove is in shaft 55 and a pin extends from sleeve 52 radially into the groove. Thus, for example, controller 12 may cause an additional, secondary, axis of motion of magnet 11, to obtain a more complicated magnetic field sensed by receiver 20 and thus, for example, to provide more information for the 6DOF calculation. Magnetometer 16 may sense the corresponding generated magnetic fields and accordingly calculate momentary phases of magnet 11, in the rotational motions about the first axis and the secondary axis, and transmit the calculated momentary phases to receiver 20.

As discussed in detail herein, receiver 20 may calculate the 6DOF position and orientation of transmitter 10 and/or receiver 20, based on sensing the magnetic field generated by transmitter 10. Receiver 20 may sense a local alternating magnetic field $M(\vec{r}, t)$, caused mostly or at least partially due to the magnetic field generated by transmitter 10, the sensed magnetic field may be describable by the following equation:

$$M(\vec{r},t)=M_0+B_x(\vec{r}(t))\cos(\varphi(t))+B_y(\vec{r}(t))\sin(\varphi(t))$$

where $\varphi(t)$ is the momentary phase of the alternating field, for example momentary phase of the rotation of the rotating magnet 11. $M_0$ is the magnetic bias which comprises of the sensor's intrinsic bias (which may slowly drift over time) plus environmental fields (such as Earth's DC magnetic field). $B_x$, $B_y$ are the magnetic fields due to the transmitter's 'x' and 'y' virtual coils, i.e. the magnetic field components in two orthogonal directions of the magnetic field as generated at and/or by transmitter 10, sensed in the current position and orientation of the receiver relative to the transmitter. In some embodiments of the present invention, and/or in some applications, receiver 20 may mostly move slowly and/or in low frequencies relative to transmitter 10. Thus, for example, for certain periods of time or across a certain number of consecutive readings by receiver 20, it can be assumed and/or approximated that $B_x$ and $B_y$ are constant and thus, for example, can be easily extracted by solving a linear system of equations, using the corresponding phase values received by transmitter 10. In other embodiments, it can be assumed and/or approximated that $B_x$ and $B_y$ have a low-degree polynomial dependency on time, at least for a certain period of time or across a certain number of consecutive readings by receiver 20. In other embodiments, processor 24 may use an extended Kalman filter which assumes a physical motion model (Newtonian motion)

which explains the sensor readings and results in a smooth and accurate real-time motion reconstruction, as further explained below.

According to some embodiments of the present invention, receiver 20 is configured to correct drifting bias $S_0$, e.g. a slowly varying sensor bias, of magnetometer 23a. In some embodiments, processor 24 decomposes the magnetic bias $M_0$ into two components:

$$M_0 = S_0 + B_0$$

Wherein $S_0$ is the slowly varying sensor bias and $B_0$ is the environmental magnetic field. When receiver 20 changes its orientation, processor 24 may distinguish these two components, for example since the environmental magnetic field in the receiver's coordinate system rotates according to its orientation while $S_0$ remains substantially constant. Processor 24 may obtain an orientation matrix U of receiver 20 relative to world coordinates, for example by integration of the readings of gyroscope 23b. Thus, for example, the magnetic bias can be written as:

$$M_0 = S_0 + U^t D_0$$

Where $D_0$ is the environmental magnetic field in world coordinates.

In some embodiments of the present invention, for a given position $\vec{r}$ and orientation matrix R of receiver 20 relative to transmitter 10, e.g. in coordinates of the transmitter, and assuming that the magnetic field generated by transmitter 10 can be modeled as magnetic dipoles with magnetic moment m, the sensed magnetic fields $B_x$ and $B_y$ can be described by the dipole equations $$B_x = R^t D_{m\hat{x}}(\vec{r}), B_y = R^t D_{m\hat{y}}(\vec{r})$$

wherein $D_{m\hat{x}}(\vec{r})$ and $D_{m\hat{y}}(\vec{r})$ are the well known formulae for magnetic dipoles $m\hat{x}$ and $m\hat{y}$ corresponding to the 'x' and 'y' virtual coils of the transmitter. The above amounts to six equations which can be solved for the 6DOF (full position and orientation) of receiver 20 and/or the transmitter 10.

In order to improve the robustness of the solution, additional information may be used: The gravity vector $G_{rx}$ in receiver coordinates, which can be extracted by sensor fusion of the accelerometer 23c and gyroscope 23b of receiver 20 using well-known methods, provides partial orientation of receiver 20. In conjunction with the gravity vector $G_{tx}$ in transmitter coordinates, sensed by the IMU 17 that is fixed with respect to rotating magnet 11, which is optionally computed in similar sensor fusion methods, an additional constraint on the orientation of receiver 20 relative to transmitter 10 is imposed:

$$G_{rx} = R^t G_{tx}$$

This yields three more equations for the orientation of receiver 20. The overall nine equations can be solved by many non-linear methods, such as Gradient-Descent, Nelder-Mead, Trust Region, Levenberg-Marquardt, real-time Kalman filter, etc.

According to some embodiments of the present invention, generator 10 and/or receiver 20 may integrate gyroscope readings of IMU 17 and/or sensor bundle 23 over short periods of time, to compute short-term fully tracked orientation of generator 10 and/or receiver 20, respectively. Accordingly, an orientation of the receiver relative to the generator over a short period of time may be calculated. The short term relative orientation may be used to enhance the accuracy of the momentary orientation calculation described in detail herein.

In certain real-time applications, such as games or VR applications that require refresh rates of 60 Hz or more, low-frequency localization of receiver 20 may not be sufficient. For this reason, sensor bundle 23 of receiver 20 and/or IMU 17 of transmitter 10 can be used for short-term localization, which captures the high-frequency motion of receiver 20 and/or transmitter 10 respectively, that may not be easily recovered based solely on the magnetic localization.

Using the gyroscope which measures angular velocity, relative orientation can be calculated by integration. Recovering linear acceleration from the accelerometer and gyroscope sensor fusion, relative position can be calculated by double integration. Both gyroscope and accelerometer usually provide sensor readings at a frequency higher than the sampling rate of the magnetometer, which can result in a smooth, highly responsive motion for a vast of applications.

However, integration produces accumulative errors (aka drift), which prevents its usage for localization over long time periods. For this reason, the low-frequency magnetic localization together with high-frequency gyroscope (orientation) and accelerometer (position) localization must be fused in a sophisticated manner. Such a fusion can be obtained by a complementary filter, in which low-frequency data is taken from one signal (the magnetic localization) and the remaining frequencies are taken from the second signal (the accelerometer/gyroscope localization). Typically, the first signal is low-pass filtered and the second signal is high-pass filtered, and the final output is the superposition of both filtered signals. In such approach, the signals must be fused in a way where frequencies are neither attenuated nor amplified (aka "All-Pass" filter). Failing to do so yields undesirable effects, such as noticeable delay or overshoot in either position or orientation.

An alternative approach for localization fusion may be an extended Kalman filter, in which the magnetic localization provides readings for position and orientation, the accelerometer and gyroscope provides readings for linear acceleration and gyroscope provides readings for angular velocities. Each input may be inaccurate (aka "noisy")—the magnetic localization may lack high motion frequencies, the linear acceleration may contain residual accelerations due to gravity, and the gyroscope may contain slowly varying bias. Nonetheless, with a carefully designed model, the Kalman filter extracts the best of each source input, and provides smooth, non-drifting 6DOF localization for receiver 20. For example, receiver 20 and/or computer device 60 may use for a Kalman filter algorithm a state vector for receiver/sensor 20. The state vector may be composed of parameters such as, for example, $S_0$, $B_0$, $\vec{r}$, Q, $\dot{\vec{r}}$, $\vec{\omega}$ which may be the magnetic sensor bias, environmental magnetic bias, position of receiver/sensor 20 in coordinates of transmitter 10, orientation in coordinates of transmitter 10 (for example, expressed as a quaternion), velocity in coordinates of transmitter 10, angular-velocity in local coordinates (not to be confused with the frequency of the transmitted magnetic field, also sometimes denoted by ω), respectively. $S_0$, $B_0$ may vary slow enough to be modeled as constant or nearly constant. Deviation from constant velocities, e.g. existence of linear and angular accelerations, and/or deviation from constant environmental magnetic field and sensor bias, can be modeled, for example, as process noise, with corresponding covariance matrices.

After defining the state vector and its dynamic model, receiver 20 and/or computer device 60 may predict a state vector of receiver 20 and/or state covariance between consecutive timeframes. Then, the state vector may be corrected according to the prediction to yield a better fit to the newly obtained sensor magnetic field reading. For example, the tracked state vector, whose magnetic measurement is modeled as M($\vec{r}$, t), may yield a vector which deviates from the latest sensed magnetic reading only by a small amount of random noise, whose standard deviation can be set according to its typical value, for example from a datasheet of the respective magnetometer.

In some embodiments, the motion model used by receiver 20 and/or computer device 60 is modular and/or extendable. For example, with the presence of optional accelerometer or gyroscope sensors, for example in receiver 20 and/or transmitter 10, the Kalman filter can be extended to include an additional state for linear acceleration, r. The accelerometer-gyroscope readings can be processed in an IMU-fusion filter to separate between gravitational acceleration and linear acceleration. The computed linear acceleration can then be fed into the Kalman filter as measurements for $\ddot{\vec{r}}$ when correcting the state vector, while the gyroscope readings can serve as measurements for $\vec{\omega}$. The accelerometer-gyroscope readings may significantly reduce the filter's latency and provide higher-rate, more stable localization.

In another configuration, for example instead of separating between "classical" IMU-fusion orientation tracking and magnetometer-based 6DOF tracking, additional IMU data (accelerometer, gyroscope) can be combined with magnetometer readings in a single unified extended Kalman filter. The states of this filter may be: $S_0$, $B_0$, $\vec{r}$, Q, $\dot{\vec{r}}$, $\vec{\omega}$, $\ddot{\vec{r}}$ (as explained above). This unified filter may use a constant (or damped) acceleration model for its position. Sensor 20 (magnetometer, optional accelerometer & gyroscope) may contribute a measurement for the "update" step, in which all measurements need to be explained using the filter's states. For example, magnetic measurements may be explained with M($\vec{r}$, t) using $S_0$, $B_0$, $\vec{r}$, Q, accelerometer measurements (which are a superposition between gravitational acceleration and linear acceleration) may be expressed by combining Q, $\ddot{\vec{r}}$, and gyroscope measurements can be explained directly by $\vec{\omega}$.

Using an extended Kalman filter for solving for 6DOF localization of sensor 20 can be easily generalized for any type of transmitter 10, not limited to the transmitter 10 described with reference to FIG. 2. As long as each magnetic measurement can be explained using the states of the filter, the filter may be fully functional and provide fast and accurate 6DOF solutions. This is an excellent property of the extended Kalman filter, where all is needed for high-quality solutions of the states is to be able to model the measurements using those states.

For example, M($\vec{r}$, t) can be replaced with any other suitable formula, depends on the magnetic field generated by the transmitter 10 being used. This makes the use of an extended Kalman filter for a 6DOF localization solution of sensor 20 invariant to the choice of transmitter, which is extremely powerful and flexible for many general uses.

In some embodiments of the present invention, computer device 60 and/or processor 24 of receiver 20 may receive and/or calculate a parametric motion model of the changes over time of the 6DOF position and orientation of receiver 20 relative to generator 10. Computer device 60 and/or processor 24 may calculate several possible time sequences of 6DOF states of receiver 20, each sequence is calculated by a different set of parameter values of the parametric motion model. For each set of parameters, and 6DOF state sequence, computer device 60 and/or processor 24 may simulate which values of sensed variables, for example variables sensed by sensor bundle 23 such as, for example, magnetic field, gravity vector, linear acceleration and angular velocities, correspond to the set of parameters and the calculated position sequence. The simulated sensed variables that are closest to the actual sensor measurements are selected, and the corresponding calculated possible sequence of 6DOF states, is identified and/or used as the 6DOF state of receiver 20 relative to generator 10. Allowing just a subspace of possible motion sequences (the "motion manifold") is beneficial for eliminating impossible or improbable motions such as overshoot artifacts etc. Constructing the restricted motion manifold can be done by relying on physical models (for example, Newtonian), or by learning methods over a database of many possible "natural" movements. An optimal localization filter would search the motion manifold for a short-term motion profile, which best matches the values sensed by all sensors combined: accelerometer, gyroscope, magnetometer, relying on transmitted and/or obtained momentary phase. A motion profile which explains all observed measurements may reflect the actual motion which took place. Searching the motion manifold consists of simulating sensor readings based on motion-profile candidates and comparing them to the actual observed measurements, relying on known noise models. Convergence can be achieved by various optimization methods as mentioned above such as Gradient-Descent, Nelder-Mead, Trust Region, Levenberg-Marquardt, real-time Kalman filter, etc.

Some embodiments of the present disclosure may include a system, a method, and/or a computer program product. The computer program product may include a tangible non-transitory computer readable storage medium (or media) having computer readable program instructions thereon for causing a processor to carry out aspects of the present disclosure. Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including any object-oriented programming language and/or conventional procedural programming languages.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

The terms 'processor' or 'computer', or system thereof, are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'software', 'program', 'software procedure' or 'procedure' or 'software code' or 'code' or 'application' may be used interchangeably according to the context thereof, and denote one or more instructions or directives or electronic circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function (s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A magnetic localization system comprising:
    a. a magnetic field generator comprising:
        i. a transmitter configured to generate at least one alternating magnetic field, and
        ii. at least one sensor at a fixed position relative to said transmitter and configured to make repeated measurements which indicate a momentary phase of the at least one alternating magnetic field;
    b. a receiver comprising a magnetometer configured to make repeated measurements which indicate a local magnetic field including the generated at least one alternating magnetic field as a component; and
    c. at least one processor configured to calculate a position and orientation of the receiver relative to the generator, based on the measured local magnetic field including the generated at least one alternating magnetic field and the measurements which indicate the momentary phase;
    wherein one or both of the measurements which indicate momentary phase and the measurements which indicate local magnetic field is associated with clock data communicated within the system;
    wherein the processor is configured to determine correspondences in time between the measurements which indicate the local magnetic field and the measurements which indicate momentary phase of the at least one alternating magnetic field, using the clock data; and
    wherein the processor uses the correspondences in time to determine a momentary phase value used with each local magnetic field measurement to calculate the position and orientation of the receiver relative to the generator.

2. The system of claim 1, comprising a sensor bundle having a gyroscope and an accelerometer, and configured to provide readings indicative of an orientation of at least one of the receiver and the generator, and wherein the at least one processor is configured to calculate a 6DOF position and orientation further based on the readings.

3. The system of claim 1, wherein the at least one processor is configured to calculate a 6DOF position and orientation by:
    extracting from the sensed magnetic field the local magnetic fields that are due to magnetic field components in at least two directions of the generated magnetic field as generated by the generator; and
    finding the position and/or orientation of the receiver by finding a unique solution for these extracted magnetic fields.

4. The system of claim 1, wherein the magnetic field generator comprises:
    an actuator configured to apply a rotational motion;
    at least one magnet rotating about a first axis by the actuator;
    said at least one sensor configured to provide said measurements which indicate said momentary phase of the at least one magnet; and
    a controller configured to control rotation of the at least one magnet to produce the at least one alternating magnetic field.

5. The system of claim 1, wherein the clock data comprises a timestamp associated with the sensed momentary phase.

6. The system of claim 2, wherein the system uses the readings indicative of the orientation to calculate at least one of a gravity vector, a linear acceleration and an orientation.

7. The system of claim 4, wherein the generator includes a processing unit configured to track the momentary phase of the at least one rotating magnet.

8. The system of claim 4, wherein the generator is configured to:
measure the at least one alternating magnetic field as it is generated by cyclic motion of the at least one rotating magnet, using the generator's magnetometer;
calculate parameters of the at least one alternating magnetic field, based on the measurements from the generator's magnetometer; and
determine a momentary phase of the at least one alternating magnetic field based on the calculated parameters.

9. The system of claim 4, wherein the at least one processor is configured to predict a value of the momentary phase corresponding to a relatively later local magnetic field measurement by the receiver, based on one or more relatively earlier momentary phase measurements by the generator, and the clock data.

10. The system of claim 4, wherein the actuator comprises:
at least two electromagnets configured to cause a rotational motion of the at least one magnet by their applied torque, wherein the applied torque is exerted through interaction of magnetic fields generated by the at least two electromagnets with magnetic fields of the at least one magnet; and
a microcontroller to control electromagnetic fields produced by the at least two electromagnets for regulated rotation.

11. The system of claim 4, wherein the actuator comprises at least one of a list consisting of a DC motor, a fluid driven rotation mechanism, air turbine, hydraulic motor, a combustion engine, a stepper motor, and a steam engine.

12. The system of claim 4, wherein the at least one magnet is further rotated about a second axis and the generator sensed by the magnetometer the corresponding generated magnetic fields and accordingly calculates momentary phases of the at least one magnet, in the rotational motions about the first axis and about the second axis.

13. The system of claim 1, wherein the receiver detects low-frequency position and orientation data by a magnetometer and high-frequency position and orientation data by a gyroscope and/or accelerometer of the receiver and/or transmitter.

14. The system of claim 1, wherein the at least one processor uses an extended Kalman filter, in which a magnetic localization provides readings for position and orientation, and an accelerometer and/or a gyroscope provide readings for gravity orientation, linear acceleration and/or angular velocities.

15. The system of claim 1, comprising a wireless communication device configured to provide a wireless communication interface between the processor and at least one of the generator and the receiver, over which at least one of the clock data, momentary phase measurements and the local magnetic field measurements is communicated.

16. The system of claim 2, wherein the sensor bundle is included within a mobile computing device as part of an inertial measurement unit, and also includes the magnetometer.

17. The system of claim 9, wherein, to predict a relatively later value of the momentary phase, the at least one processor is configured to:
receive receiver clock timestamps and transmitter clock timestamps;
identify a time relation between the receiver clock and the transmitter clock, based on their respective timestamps;
convert a receiver clock value to a transmitter clock value based on the identified time relation; and
calculate the phase, based on the relatively earlier momentary phase measurements and the converted transmitter clock value.

18. The system of claim 1, wherein the momentary phase measurements and the local magnetic fields measurements are communicated to the processor with one or more of different relative latencies and changing relative latencies.

19. A method of performing magnetic localization, comprising:
receiving, at a processor:
data of a first type comprising momentary phase values, which indicate a momentary phase of the at least one alternating magnetic field, measured for an at least one alternating magnetic field produced by a transmitter in an alternating magnetic field generator, said indication of a momentary phase being measured by at least one sensor located at a fixed position in said alternating field generator relative to said transmitter;
data of a second type comprising magnetic measurement values, which indicate a local magnetic field including the at least one alternating magnetic field, measured at a receiver comprising a magnetometer, and
clock data indicative of times of the measurements, and respectively associated with measurement values of each of the first and second types; and
calculating, using the processor, positions and orientations of at least one receiver relative to the generator, based on the data of the first and second types, and their respectively associated clock data.

20. The method of claim 19, wherein the receiving data of the first type from the generator occurs with a difference, compared to the receiving data of the second type from the receiver, in one or more of: a latency, a random stall, and a data loss.

* * * * *